(12) United States Patent
Wyss et al.

(10) Patent No.: US 9,724,267 B2
(45) Date of Patent: Aug. 8, 2017

(54) CONTAINER FOR STORING MEDICAL OR PHARMACEUTICAL LIQUIDS

(71) Applicants: Martin Wyss, Rotkreuz (CH); Rudolf Zihlmann, Langnau (CH); Gerald Studer, Flaach (CH); Andreas Geipel, Oftringen (CH); Davide Crotta, Cadenazzo (CH)

(72) Inventors: Martin Wyss, Rotkreuz (CH); Rudolf Zihlmann, Langnau (CH); Gerald Studer, Flaach (CH); Andreas Geipel, Oftringen (CH); Davide Crotta, Cadenazzo (CH)

(73) Assignee: Roche Diagnostics International AG, Rotkreuz (CH)

( * ) Notice: Subject to any disclaimer, the term of this patent is extended or adjusted under 35 U.S.C. 154(b) by 815 days.

(21) Appl. No.: 13/894,834

(22) Filed: May 15, 2013

(65) Prior Publication Data

US 2013/0253439 A1    Sep. 26, 2013

Related U.S. Application Data

(63) Continuation of application No. PCT/EP2011/066753, filed on Sep. 27, 2011.

(30) Foreign Application Priority Data

Nov. 15, 2010 (EP) .................................... 10191221

(51) Int. Cl.
*A61J 1/14* (2006.01)
*A61M 5/172* (2006.01)
(Continued)

(52) U.S. Cl.
CPC . *A61J 1/14* (2013.01); *A61J 1/05* (2013.01); *A61M 5/172* (2013.01); *A61M 5/38* (2013.01)

(58) Field of Classification Search
CPC .. A61J 1/14; A61J 1/05; A61M 5/172; A61M 5/38
See application file for complete search history.

(56) References Cited

U.S. PATENT DOCUMENTS

| 4,294,594 A | 10/1981 | Sloane, Jr. et al. |
| 4,515,606 A * | 5/1985 | de Winter ............. A61M 5/385 96/6 |

(Continued)

FOREIGN PATENT DOCUMENTS

| EP | 1970677 A1 | 9/2008 |
| EP | 2163273 B1 | 4/2013 |

(Continued)

*Primary Examiner* — Theodore Stigell
(74) *Attorney, Agent, or Firm* — Woodard, Emhardt, Moriarty, McNett & Henry LLP (57) ABSTRACT

A container for storing a medical or pharmaceutical liquid comprising a storage compartment for storing the liquid comprising, an inlet opening for filling the storage compartment and an outlet opening for discharging liquid out of the storage compartment is presented. A hydrophilic membrane layer is arranged within the storage compartment which is gas-tight in a wet condition and which at least covers the outlet opening and contacts the liquid stored within the storage compartment. A dosing assembly and a device for automated release of a medical or pharmaceutical liquid comprising and/or capable of using at least one container are also disclosed.

20 Claims, 6 Drawing Sheets

(51) Int. Cl.
    *A61J 1/05*     (2006.01)
    *A61M 5/38*     (2006.01)

(56) References Cited

U.S. PATENT DOCUMENTS

| | | | |
|---|---|---|---|
| 5,006,050 A * | 4/1991 | Cooke | A61M 5/14224 |
| | | | 417/478 |
| 7,419,484 B2 | 9/2008 | Schiltges et al. | |
| 7,955,302 B2 | 6/2011 | Haueter et al. | |
| 2002/0128603 A1 * | 9/2002 | Booth | A61B 17/3421 |
| | | | 604/164.01 |
| 2006/0124458 A1 * | 6/2006 | Nauber | G01N 27/404 |
| | | | 204/424 |
| 2006/0184119 A1 | 8/2006 | Remde et al. | |
| 2007/0049865 A1 | 3/2007 | Radmer et al. | |
| 2007/0203454 A1 | 8/2007 | Shermer et al. | |
| 2008/0051710 A1 | 2/2008 | Moberg et al. | |
| 2009/0105685 A1 | 4/2009 | Stroem Hansen et al. | |
| 2010/0234824 A1 | 9/2010 | Huwiler et al. | |

FOREIGN PATENT DOCUMENTS

| | | | |
|---|---|---|---|
| GB | 1221625 | * | 2/1971 |
| GB | 1 452 104 | | 10/1976 |
| GB | 2000685 | A | 1/1979 |
| JP | H09500809 | A | 1/2001 |
| JP | 2010501277 | A | 1/2010 |
| WO | 9503842 | A1 | 2/1995 |
| WO | 2004/009162 | A1 | 1/2004 |
| WO | 2005000580 | A1 | 1/2005 |
| WO | 2010/063424 | A1 | 6/2010 |
| WO | 2010/105718 | A2 | 9/2010 |

* cited by examiner

CONTAINER FOR STORING MEDICAL OR PHARMACEUTICAL LIQUIDS

CROSS-REFERENCE TO RELATED APPLICATIONS

This application is a continuation of PCT/EP2011/066753, filed Sep. 27, 2011, which is based on and claims priority to EP 10191221.0, filed Nov. 15, 2010, which is hereby incorporated by reference.

BACKGROUND

The present disclosure generally relates to a container for storing a medical or pharmaceutical liquid, in particular for storing an insulin preparation, which is administered to a patient by, for example, an infusion pump. Further the present disclosure generally relates to a dosing apparatus for dosing a predetermined amount of liquid from the container and a device for automated release of the medical or pharmaceutical liquid from the container.

Devices for the automated release of medical or pharmaceutical liquids are normally used with patients who have a continuous and, in the course of the day, varying need of medicine, which can be administered by subcutaneous or intravenous infusion. Some applications are, for example, certain pain therapies and the treatment of diabetes, in which computer controlled infusion pump devices, such as insulin pumps, are used. Such devices can be carried by a patient on the body and contain a certain amount of liquid medicine in a liquid reservoir, for example, in the form of a container. The liquid reservoir often comprises medicine sufficient for several administrations on one or several days. Such a device may comprise a dosage unit or is connected to a dosing unit for controlling the required amount of liquid and providing it for administration. The administration may be continuous or a repeated dispense of predetermined amounts of liquid. The liquid medicine is supplied to the patient's body from the medicine reservoir through an infusion cannula or an injection needle. Additional tubing may be present between liquid reservoir and cannula or needle.

Infusion devices are, for example, a modular infusion pump device or an infusion device with a down stream pump system. One system for the delivery of a substance can have a dosing unit for withdrawal of a specified amount of liquid from a reservoir, for example, in the form of a cartridge or a bag. The system uses the same opening for bringing in the liquid amount from the reservoir and for administering the same to a patient. Another system can have a fluidic assembly comprising a dosing unit and a drug reservoir for an ambulatory infusion device. The dosing unit comprises a charging and discharging valve system, wherein the drug reservoir is in fluid connection with an inlet valve thereof. The drug reservoir may be realized as a cartridge, a bag, a pouch or the like.

Particularly in self-administration medicine, for example, insulin, the patients using the medicine in question and administering it themselves by an infusion pump are increasingly emphasizing convenience and discretion. As a consequence, the dimensions of such infusion devices are limited, and, in particular, the overall length, width and thickness should be as small as possible in order not be evident through clothing and to be carried as comfortably as possible.

While there are fully or partly disposable single-use infusion pump devices, such devices are typically non-disposable and are loaded with a disposable drug reservoir.

As drug reservoirs, rigid containers like cartridges are commonly used. Also flexible containers like bags are suitable, which may comprise two flexible wall sheets sealed together or one flexible sheet in combination with a rigid shell. Disposable containers are preferable for sterility and contamination-prevention reasons. They may be delivered prefilled with a certain medical or pharmaceutical liquid, or empty, ready to be filled by a user. Self-filling of containers has the advantage that medicines that are not readily available in prefilled containers can be used in infusion pump devices, thereby providing the patient with a larger choice of sources for his medicines. Furthermore, the stability of many medicine in liquid form, particularly in plastic containers, is limited.

Flexible containers have the advantage of a smaller volume surplus of the container in relation to its content, which reduces the costs of manufacture and the achievable dimensions of an infusion pump device. For use in an infusion pump device, a flexible container is connected to a conduit system of the device, especially to a dosage unit of the device. For that purpose the flexible container may be provided with a port. Such a port can be mounted an the container with a flange sealed to a container wall sheet. Or, a port in the form of a flexible tube or rigid connection piece welded between two sheets of the container at the periphery of the flexible container may be used.

A medical device using a flexible container can house a flexible drug reservoir with a port closed by a septum that is punctured by a hollow needle of the conduit system of the infusion pump device. An infusion device comprising a fluid reservoir made of a rigid bladder shell and a non-distensible bladder film welded thereto where the content of the reservoir is dispensed by a spring force through one or more flow paths in fluid connection to the reservoir.

A common problem of flexible containers with ports is the dead volume remaining between the collapsed container and the port. Thus, complete drainage of the contents of a flexible container is not possible. For a single-use container filled with the medicine, the dead volume considerably increases the effective cost per dose and thus of the overall therapy cost. Additionally the dead volume leads to an increase of the overall volume of the flexible container, and thus of an infusion pump device that utilizes such a flexible container.

A further problem, particularly of flexible containers as they are known, is air remaining in the container. If, for example, a flexible container is provided empty and is intended to be filled with the appropriate medicament by the user himself, the dead volume is initially filled with air. However, removing the air from flexible containers will require a certain skill level of a user. In addition to air resulting from the dead volume of the container, some amount of air may enter the container when being filled, typically by a user prior to usage, as described above.

Furthermore, many drugs and in particular insulin are typically stored at low temperature, for example, in a refrigerator. When being used in an administration device or infusion device at a higher temperature, such as room or body temperature, air that is initially solved in the liquid outgases, resulting in air bubbles inside the container.

In current devices, air bubbles may be administered instead of the liquid medicine, which leads to potentially dangerous dosing errors. Furthermore the administration of air into a patient's body should generally be avoided for medical reasons.

Furthermore, most devices monitor a pressure or force applied during drug release by a drive in order to detect the presence of fluidic occlusions or blockages. Due to the negligible compressibility of liquids, the fluidic pressure tends to show a steep increase in such situations. Air or generally gas, however, has a high compressibility and therefore drastically reduced the fluidically stiffness. Therefore, the pressure increase and the detection of occlusions or blockages are largely delayed.

Often the problems of dead volume areas and air remaining in the container amplify each other when a container is orientated in an unfavorable position; for example, when a port is located in an upper part while liquid converges in a lower part of the container such that a fluid connection between port and liquid is interrupted.

Therefore, there is a need for a container for storing medical or pharmaceutical fluid, which enables save discharge of fluid from the container, largely avoids administration of air from the container, guarantees easy handling and safe storage of liquid within the container, offers high flexibility and convenience for a patient using the container, and is produced at low cost, which improves precise dosing of liquid, is easy to handle and may be produced cost-efficient and which enables simple maintenance and handling, improves liquid administration of precise dosages, and offers comfortable usage for a patient.

SUMMARY

According to the present disclosure, a container for storing a medical or pharmaceutical liquid is presented. The container can comprise a storage compartment for storing the liquid comprising an outlet opening for discharging liquid out of the storage compartment; and a hydrophilic membrane layer within the storage compartment which is gas-tight in a wet condition and covers the outlet opening. The membrane layer can contact the liquid stored within the storage compartment independent of a container orientation with respect to gravity and a filling level of the container.

In accordance with one embodiment of the present disclosure, a dosing assembly comprising the container and a dosing unit is also presented.

In accordance with another embodiment of the present disclosure, a device for automated release of a medical or pharmaceutical liquid, particularly an infusion pump device can comprises and/or capable of using the at least one dosing assembly is also presented. The device can further comprise control circuitry and a drive unit coupled to the container or the dosing assembly during application. The control circuitry can operatively be coupled to the drive unit, thus controlling automated drug release of the container.

Accordingly, it is a feature of the embodiments of the present disclosure to provide a container for storing medical or pharmaceutical fluid, which enables save discharge of fluid from the container, largely avoids administration of air from the container, guarantees easy handling and safe storage of liquid within the container, offers high flexibility and convenience for a patient using the container, and is produced at low cost, which improves precise dosing of liquid, is easy to handle and may be produced cost-efficient and which enables simple maintenance and handling, improves liquid administration of precise dosages, and offers comfortable usage for a patient. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A container for storing a medical or pharmaceutical liquid can comprise a storage compartment for storing the medical or pharmaceutical liquid and an outlet opening for discharging liquid out of the storage compartment. In some embodiments, the container may comprise an inlet opening for filling the storage compartment. The inlet opening and the outlet opening can mostly be separate openings in the container. But they could also be realized as one single opening, which may be used for filling and for subsequently discharging a liquid. In a further alternative, no dedicated inlet opening may be present and the liquid can be directly filled in during manufacture of the container. A hydrophilic membrane layer within the storage compartment, which is gas-tight in a wet condition, can cover at least the outlet opening and contacts the liquid stored within the storage compartment. In other words, the liquid within the storage compartment can be in fluidic connection with the outlet opening via the membrane layer. In practice, the hydrophilic property of the membrane layer can attract liquid stored in the storage compartment and therefore the membrane layer can be in a wet condition as long as there is liquid in the storage compartment. Even if only some parts or small areas of the membrane layer are in contact with the liquid, the whole membrane layer can be saturated with liquid since the membrane material can attract the liquid because of its hydrophilic property. The liquid stored in the storage compartment can contact the membrane substantially independent of a container orientation with respect to gravity and a filling level of the container. Therefore any air, or other gas, within the liquid filled container cannot pass the outlet opening and can remain in the storage compartment.

The container can mainly be intended for use in a dosing assembly comprising at least one container and a dosing unit. The dosing unit can be between the outlet opening and an injection needle or infusion cannula. Container and dosing unit can be releasably, or permanently, connected and may form a compact integral unit in some embodiments. Alternative, more than one container as disclosed can be used with a dosing assembly. The container can also be used in a device for automated release of the medical or pharmaceutical liquid of the container, in particular an infusion pump device.

The container can prevent air, which might be present in the storage compartment, from leaving the container and entering components, such as a dosing unit, downstream of the container. Thus, reliability of the function and the stability of a dosing assembly or a device for automated release of the liquid from the container may be improved. The container and therefore a dosing assembly and a device for automated release of the liquid, which may use such a container, can have a compact, non-bulky structure, since the hydrophilic membrane layer can be positioned inside the storage compartment and can be designed as a flat and thin layer.

To diminish the dead volume within flexible containers for use in an infusion pump device for administration of medical or pharmaceutical liquids container structures are proposed. These flexible containers comprise a wall comprising two wall sheets of flexible material that are sealed together and encompass a storage compartment for a liquid medicament. An access opening in connection with the storage compartment is provided in one of the wall sheets for fluid connection to a dosing unit or an infusion pump device. The container comprises a fluid channel arranged between the storage compartment and the access opening, which is formed by a cavity in one or both of the two wall sheets. The cavity is formed as an oblong corrugation or groove in one of the sheets. An insert part is arranged between the two wall sheets with positive locking and fluidly connects the storage compartment and the access opening instead of the fluid channel.

Typically, a container can be provided hermetically closed and sealed to keep the inside of the container sterile. The container can be provided either completely or partially filled with a medical or pharmaceutical liquid or can be empty. While re-filling of the container may be possible, the container can often be designed as single-use device which can be discarded when empty for handling as well as sterility reasons.

The membrane layer can be attached an inner surface of the storage compartment at least around the outlet opening. The membrane layer may be attached on its circumferential edge to the inner surface of the storage compartment such that the membrane layer can be fixed at the surface. Alternatively, for example, in case of an elongated membrane layer the layer may be spun across the interior volume of the storage compartment; for example, one end of the membrane layer can be fixed around the outlet opening and the opposite end can extend through the inner volume of the storage compartment or even can be attached inside the storage compartment. The attachment can be gas-tight at least around the outlet opening to prevent gas passing through the attachment from the storage compartment in direction of the outlet opening. The membrane layer can be attached to the surface by common joining methods. For example it can be welded, for example, by ultrasonic, laser or thermal sealing methods or by standard mechanical joining methods. Attention can be paid not to block a fluidic passage through the membrane layer by attachment or joint materials or layers. There can always remain a contact area an the membrane layer for contact with liquid and a contact area open to the outlet opening. The formation of liquid sections within the storage compartment, which are not in contact with the membrane layer, can be avoided.

Thus advantageously the membrane layer can extend at least along about 50% of a length of the storage compartment at least in one dimension. In one embodiment, it can extend along about 80%, or even along close to approximately 100% of the length of the storage compartment in at least one dimension. An extensive widespread inner surface area of the storage compartment may be covered by the membrane layer or even a complete surface side of the storage compartment may be covered with the membrane layer. But it has to be taken into account, that a volume of the membrane, that is, volume of pores of the membrane, can represent a dead volume, on one hand, containing air before it is liquid filled, and on the other hand, for keeping the medical liquid, which can mean a loss of the medical liquid. Therefore advantageously, the surface cannot be fully covered. Furthermore, typical suited membrane materials can be comparatively expensive. Nevertheless the basically outermost points or sections of the storage compartment can be in contact with the membrane layer.

The membrane layer can for example be realized in an elongated narrow and flat form, for example, as a strip or band. The membrane layer may be designed in a star, or cross, geometry comprising several strip arms. Also the membrane layer may comprise more than one strip, wherein the strips can be connected with each other, for example they can be crossed with each other close to the outlet opening. The storage compartment as well may comprise an elongated form, for example, oval or rectangular form. The storage compartment advantageously may be designed with rounded corners. Thus a membrane layer strip or strips may stretch out along the longitudinal form of the storage compartment, for example, straight, diagonal, in a waved, annulated or zigzag shape, or other geometry. In general, the geometry of the membrane layer layout within the storage compartment can be optimized such that the dead volume within the membrane can be minimized and the accessibility of the membrane layer for the liquid is maximized, for example, the distance of compartment sections to the membrane layer can be as short as possible. Thus, the membrane layer can be kept in a wet condition at all times and gas can be prevented from passing the outlet opening.

In one embodiment, for example, the membrane layer can comprise at least one membrane strip running essentially along a center line of the storage compartment. The edge of the membrane strip can be welded on an inner surface of the storage compartment. In case of an elongated container, the outlet opening may be located in a first half or first end area of the storage compartment, while the membrane strip can stretch from this first half to the adjacent second half or second end area along the longitudinal axis of the storage compartment. In an advantageous layout, the membrane strip can extends along at least about 80% of the longitudinal size of the storage compartment. Thus, it can be only a short distance to the membrane layer from any section within the storage compartment. The hydrophilic character of the membrane layer can attract liquid form all sections to flow towards the membrane layer and the membrane layer can be maintained in a wet state.

In another embodiment, the membrane layer layout can comprise a cross shaped geometry, which can run essentially diagonal through the storage compartment and can contain a cross point in a middle area of the storage compartment. In this case, the storage compartment may comprise a square shape or even a quadratic shape and the outlet opening may be located in the cross point of the membrane layer layout. Again all sections of the storage compartment can be in close distance to the membrane layer and also to the outlet opening. Nevertheless the surface area of the membrane layer can be kept small. Thus the dead volume within the membrane layer can be reduced and all liquid areas and sections of the storage compartment can be linked to the membrane layer.

Such a geometry of the container and membrane layer layout within the storage compartment can allow safe contact of the liquid with the membrane layer in any orientation of the container. The liquid stored in the storage compartment can contact the membrane substantially independent of a container orientation with respect to gravity and a filling level of the container. It may not be relevant which side of the container is up or down or if the container is in an oblique position because, in any case, at least one area of the membrane layer can be in contact with liquid, which usually tends to flow down inside the container because of gravity. Thus the membrane layer can be continuously in a wet condition substantially irrespective of the orientation of the container. This can ensure that air can be retained within the storage compartment independent of different application habits of different patients and can guarantee reliable function of a dosing assembly or a device for automated release of the liquid as mentioned before.

The hydrophilic membrane layer can be made of porous membrane material. For example the membrane layer can be made of polyethersulphphone (PES) or cellulose acetate. The pore size of the hydrophilic membrane can determine the bubble-point of the membrane and the required pressure difference for a liquid to pass through the membrane from inside the container through the outlet opening to a connected system. The smaller the pore size, the higher can be the bubble-point. Thus the pore size needs to be small enough to avoid gas to pass through the membrane when a maximum pressure acts an the liquid, which can be generated by, for example, a dosing or administration system. On the other hand, the required pressure to expel liquid from the storage container can increase with diminishing pore size and can enhance the demands on a pressure system providing such pressure, for example, a dosing unit or an automated release device. Thus the pore size may be designed as big as possible to minimize required pressure force. Finally the pore size may be chosen in respect to the medical or pharmaceutical preparation of the liquid. The pore size may affect on the preparation negatively in case the pore size is too small. Also it can be advantageous to dimension a pore size of the membrane layer of the container in respect of a dosing or administration pressure exerted on the liquid. In one embodiment, a pore size of the membrane material can be about 0.2-1.2 pm. In another embodiment, the pore size of the membrane material can be about 0.45-0.80 pm. Such a pore size can show good administration and dosing characteristics for insulin preparations for example. In one embodiment, the thickness of a membrane layer can be for example between about 50 and 300 pm. In another embodiment, the thickness of a membrane layer can be between about between 100 and 200 pm.

The membrane layer may comprise a symmetric, or homogenous, porous structure, wherein the pore size can generally be uniform throughout the membrane layer. Also the membrane layer may comprise an asymmetric porous structure, wherein the pore size can vary within the membrane layer. Thus, the membrane layer may include differing pore sizes in specific areas of the layer. For example, it may be helpful to have smaller pores directed to the liquid side of the layer to prevent air passing though the membrane. In direction to the storage compartment side of the layer, bigger pores can ease the crossflow of liquid within the membrane layer towards the outlet opening. The membrane layer may be made of a single layer or may be realized as sandwich of two or more layers.

According to one embodiment of a container, the storage compartment can comprise an essentially rigid, or hard, wall part or wall member comprising the outlet opening and if necessary also the inlet opening, and at least one flexible or elastic wall part or wall sheet attached, in particular sealed, to the rigid wall member. Also the storage compartment may comprise two flexible wall sheets sealed together, while a rigid shell or the like supports one of them. Such a semi-flexible container or hybrid container can comprise a storage compartment with a variable volume. That can mean if the flexible wall sheet lies on the rigid wall part the internal volume of the storage compartment can be nearly zero and can increase as soon the flexible wall sheet is lifted from the rigid wall part, for example, by filling in a liquid through the inlet opening. The other way round, the volume can diminish as soon as liquid is extracted from the storage compartment. The rigid wall part can serve as a support member of the container, which can basically keep the container in an elongated non-buckled form. The membrane layer can advantageously be attached to an inner surface of the rigid wall part and therefore can be stiffened by this part. Such a container construction can ensure that the container is not accidentally twisted or flexed, which might cause separation of fluid from the membrane layer. Also such a container may need only three elements to be assembled: the rigid wall part, the flexible wall sheet and the membrane layer.

The flexible wall sheet can be produced from a plastic or synthetic foil, which also may be coated with a suitable material, for example aluminum, to enhance barrier characteristics for the liquid. The sheet like material of the flexible wall may be a monolayer film or a multilayer structure. The material may, for example, comprise one or more polymers of the following families: Polypropylene (PP), Polyethylene (PE), Ethylene Vinyl Alcohol (EVOH), Polyamide (PA), Polychlorotrifluoroethylene (PCTFE), Cyclic Olefin Copolymer (COC), Polycarbonate (PC), Ethylene Vinyl Acetate (EVA), Polyvinyl Chloride (PVC), Polyvinylidene Chloride (PVDC), Polystyrene (PS), Polyethylene Terephthalate (PET), Thermoplastic Elastomer (TPE), Polymethacrylate (PMMA/MABS/MBS) or any other suitable polymers. The flexible wall sheet may be manufactured for example by extrusion, blown film extrusion, coextrusion or lamination. When producing a multilayer structure, it may be helpful to include one or more tie layers or to apply one or more adhesive layers between the functional layers. Multilayer structures can improve the barrier properties to ensure integrity of the liquid stored inside of the reservoir and can prevent loss of preservatives. To improve barrier properties, it may also be advantageous to use metallized film or to apply a silicon oxide or aluminium oxide coating.

The rigid wall part can be an injection molded part. It may comprise a polymer of the following families: Polypropylene (PP), Cyclic Olefin Copolymer (COC), Polymethacrylate (PMMA/MABS/MBS), Copolyester (PCTG), Polyethylene Terephthalate (PET) or 25 Polycarbonate (PC).

Advantageously, the rigid wall part and the flexible wall sheet can be made of synthetic material of the same family. They can be joined by the same methods as used for the attachment of the membrane layer as described above.

In another embodiment, the container can comprise two flexible wall sheets, which can be sealed together such that the storage compartment can be encompassed by the flexible wall sheets. The inlet opening may be formed in a first wall sheet and the outlet opening can be formed in a second wall sheet. In this case, a flexible membrane material can be chosen for the membrane layer and can be attached at least around the outlet opening. Thus, the shape of the container can be very flexible and the container easily can fit into place in a specific dosing assembly or device for automated release of the liquid.

It can be an advantage of a container comprising at least one flexible wall sheet, as compared to rigid cartridges with plunger, that the container can have any desired shape and be placed at any position and in any orientation in the device.

A container may comprise a channel structure, which can be arranged in or on the surface of the storage compartment, to which the membrane layer can be attached. The channel structure can be in fluidic connection with the outlet opening. It can help to collect liquid in flow direction behind the membrane layer or within the membrane layer and to direct the liquid to the outlet opening. The channel structure may be realized by a groove or a groove network embedded into the surface of the storage compartment leading to the outlet opening. Alternatively, the surface of the storage compartment can be a generally rough or structured surface, such that irregularities or recesses in the surface can form a channel structure when the membrane layer is attached to the surface and can seal the covered surface area of the storage compartment in relation to the interior of the storage compartment. Such a channel structure can be fully covered by the membrane layer and can be sealed to the interior of the storage compartment in a gas-tight manner.

The channel structure can be realized by a porous structure or the porosity of the membrane material itself. That can mean that the pores of the membrane layer can be linked such that a passage way can be formed within the membrane layer, which can reach from the contact area of the membrane layer in contact with the liquid to the outlet opening.

In this case, the membrane layer can be attached on a smooth, in particular polished, inner surface of the storage compartment. The channel structure can assist the transport liquid without any gas through the outlet opening. As mentioned before, the membrane material may comprise a varying pore size such that the pore size towards the inner surface of the storage compartment can be large than towards the liquid side. In case of a porous passage way as channel structure, the amount of liquid enclosed in the channel structure can be minimized and therefore the amount of liquid remaining in the container, which may not be expelled from the container, can be minimized as well. Also gas which is present in the channel structure between the entrance of liquid into the membrane and the outlet opening, before liquid has entered the membrane layer a first time, can be minimized.

For the connection of the container to a dosing or administration system, the container may comprise a connection port arranged on the outer side of the container and in fluidic connection to the outlet opening. The inlet port as well may be provided with a connection port. The connection ports may be designed as conventional fluid ports to realize a fluidic connection between the interior of the storage compartment and another system. The connections may be realized as mechanical fits or as friction fittings, for example, by Luer locks or the like. Mostly the connection ports can be sealed by a septum which can be pierced when the connection port is connected to another system.

According to another embodiment, a dosing assembly comprising at least one container for storing a medical or pharmaceutical liquid as described above and a dosing unit can be provided. The at least one container can be in fluidic connection with the dosing unit. The at least one container can releasably be connected to the dosing unit, such that an empty container may be replaced with a full one. Alternatively, the container may be refilled within the dosing assembly. Alternatively, both the container and the dosing unit can be discarded after use for sterility reasons. In a further embodiment, the container and the dosing unit form a single, compact unit that can be provided readily assembled. The dosing unit can extract a predetermined amount of liquid from the container. The dosing unit can be part of a device for automated release of a liquid, for example, an infusion pump device, or it may be connectable to such a device.

The dosing unit may comprise a pump chamber, such as a membrane pump chamber or a pump cylinder, and a valve that can be fluidically arranged between the outlet opening of the container and an inlet opening of the pump chamber. This valve may be controlled to be open for drawing liquid form the container into the pump chamber and to be closed for subsequently dispensing or releasing the liquid from the pump chamber. Such an arrangement can have the favorable property that the container can be fluidically decoupled from the pump chamber during delivery. Consequently, any gas or air inside the container may not effect the fluidic system and can stiffen during administration. Since air or gas are prevented from leaving a container, all fluidic conduits and cavities downstream of the container can be permanently filled with liquid. In comparison to a system without air retention, the pressure increase in case of a blockage or occlusion downstream of the pump chamber can be largely increased, thus enabling fast detection of blockages or occlusions, for example, via monitoring the pressure inside the pump chamber or, for the dosing unit comprising a piston pump, by monitoring a force exerted onto the plunger for pumping.

According to yet another embodiment, a device for automated release of a medical or pharmaceutical liquid, such as an infusion pump device comprising an administration system for administering liquid, is provided, which can comprise and/or can be capable of using at least one container as described above and/or a dosing assembly as described above. Such an infusion pump device can ensure correct administration of precisely measured dosages of a medical liquid irrespective of the orientation of the device while carried on the body of a patient. Also the dimensions of the device can be small and therefore the device can be carried inconspicuously on the body.

In use a dosing or administration pressure can be exerted on the liquid by the dosing unit or the device for automated release of the liquid. The pore size of the membrane layer of the at least one container can usually be dimensioned such that, during application, a differential pressure over the membrane layer can be below a bubble pressure of the membrane layer.

A dosing assembly and/or automated release device using the container may comprise a pumping and dosing mechanism respectively, or at least part of a pumping mechanism, such as a micro membrane pump, or a micro plunger pump. Furthermore the dosing assembly and/or the automated release device may comprise a connection device for positioning and/or fixating the at least one container by a fluidic connection with the connection port of the container. The connection device may comprise further functional elements, such as for example a pressure sensor, or a pressure transfer membrane for coupling to a pressure sensor for monitoring the fluidic pressure inside the container. The device further may comprise an electronic control circuitry and a drive unit. The drive unit can be coupled to the container or the dosing assembly during application. The control circuitry can be operatively coupled to the drive unit, thus controlling automated drug release of the container.

As used herein, the term "medical or pharmaceutical liquid" can be meant to include any drug containing flowable medicine preparation, or therapeutic or diagnostic liquid, capable of being passed through a delivery element such as a hollow needle in a controlled manner, such as a liquid, solution, gel or fine suspension. Representative drugs can include pharmaceuticals such as peptides, proteins, and hormones, biologically derived or active agents, hormonal and gene based agents, nutritional formulas and other substances in both solid (dispensed) or liquid form. In one embodiment, the medical liquid can encompass insulin preparations ready for administration.

Figure 1A:
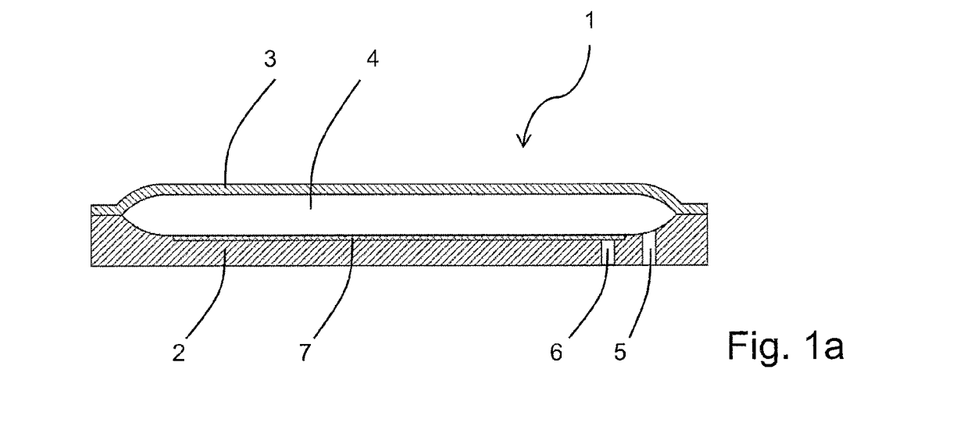
FIG. 1a illustrates cross-sectional side view of a first embodiment of a container according to an embodiment of the present disclosure.
Figure 1B:
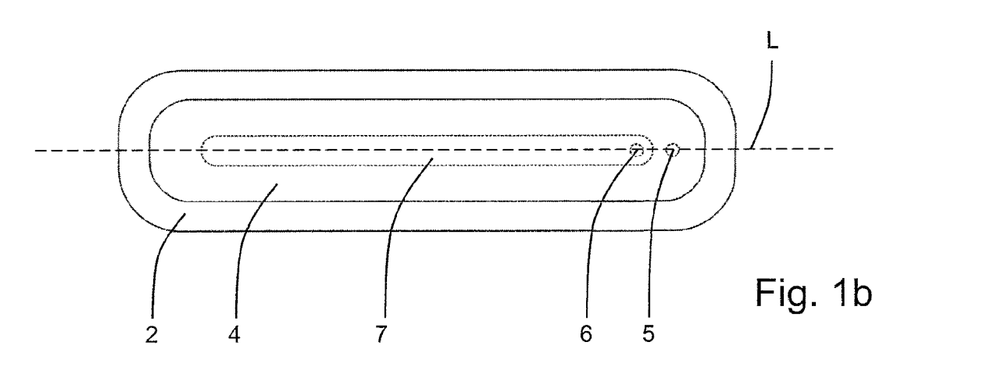
FIG. 1b illustrates top view of the container according to FIG. 1a according to an embodiment of the present disclosure.

Referring initially to FIGS. 1a and 1b, a first embodiment of a container 1 according is shown. The container 1 can comprise two wall parts. A first wall part 2 can be realized by a rigid wall part in shell-form and a second wall part 3 can be realized by a flexible wall sheet formed by a synthetic foil. The rigid wall part 2 and flexible wall sheet 3 can be joined at their respective edge such that a storage compartment 4 can be encompassed between the two wall parts 2 and 3 for storing a medical or pharmaceutical liquid. The storage compartment 4 can have a volume of about 3 ml. In the context of insulin therapy, the volume can be typically in a range of about 1 ml to about 5 ml.

The rigid wall part 2 and the flexible wall sheet 3 can be joined together for example by welding for establishing a gas- and liquid tight bonding. The rigid wall part 2 can comprise an inlet opening 5 and an outlet opening 6. The inlet opening 5 and the outlet opening 6 can be separated from each other. The outlet opening 6 can be covered by a hydrophilic membrane layer 7 attached to a surface of the rigid wall part 2 and can extend along the interior space of the storage compartment 4. The membrane layer 7 can be attached to the rigid wall part 2, for example, by ultrasonic, laser or thermal sealing methods or by standard mechanical joining methods. Also the wall parts or the membrane layer 7 may be glued together, wherein attention may need to be paid that glue material does not interact with a liquid within the storage compartment or blocks the membrane. An edge area of the membrane layer 7 can be covered by sealing material. The greater middle area of the membrane layer 7 can remain as a contact area for contact with liquid within the storage compartment 4. Also the side of the membrane layer 7 facing the surface of the rigid wall part 2 may serve as an attachment surface as long as a contact area around the outlet opening 6 stays free for fluidic contact with the outlet opening 6. In general, it can be important that at least the periphery around the outlet opening 6 is sealed towards the storage compartment 4 by the membrane attachment such that no gas or air within the storage compartment 4 can reach the outlet opening 6 directly, that is, via a bypass of the membrane layer. As shown, the membrane layer 7 can be embedded into the surface of the rigid wall part 2. The membrane layer generally can comprise a porous material like polyethersulphone or cellulose acetate, for example. In one embodiment, the porous material may have a pore size of about 0.2-1.2 pm. In another embodiment, the porous material may have a pore size of about 0.45-0.80 pm as discussed above.

In FIG. 1b, the container 1 of FIG. 1a, is shown from the top without the flexible wall sheet. The container 1 and the storage compartment 4 can have an elongated and narrow form, which can be symmetrical along a longitudinal center axis L. The membrane layer 4 can be in the form of an elongated flat membrane strip, which can run essentially straight along the center axis L of the storage compartment 4. The membrane layer strip 7 can extend at about 80% of a length of the storage compartment 4 along the dimension of the center axis L. The inlet opening 5 can also be positioned on the center axis L in an area of the storage compartment 4 not covered by the membrane layer strip 7.

Figure 2:
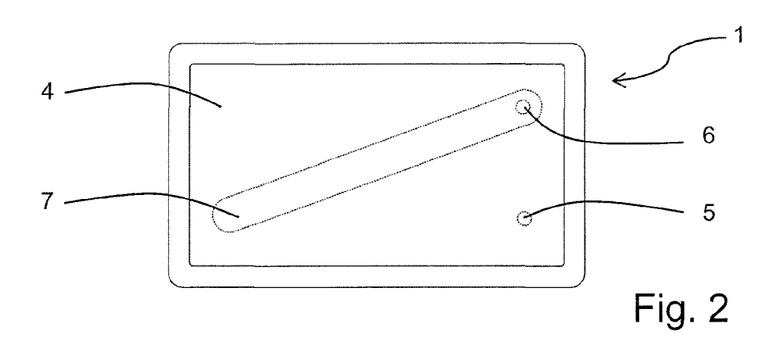
FIG. 2 illustrates top view of a second embodiment of a container according to an embodiment of the present disclosure.
Figure 3:
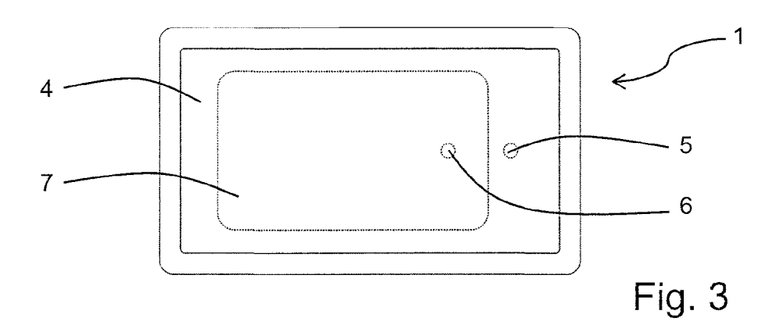
FIG. 3 illustrates top view of a third embodiment of a container according to an embodiment of the present disclosure.
Figure 4:
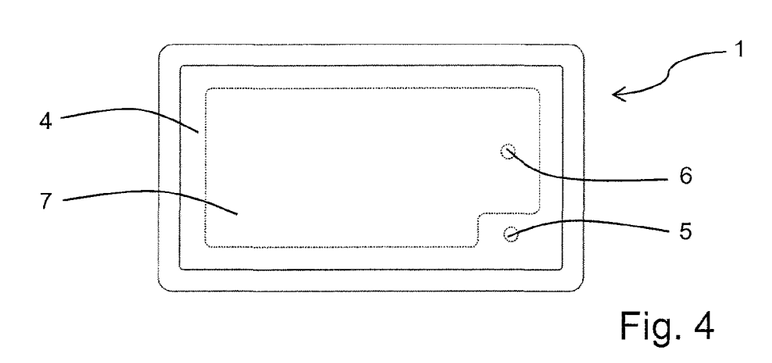
FIG. 4 illustrates top view of a fourth embodiment of a container according to an embodiment of the present disclosure.

In FIGS. 2, 3 and 4 further embodiments of a container 1 are shown in a schematical view. The container 1 and the storage compartment 4 can respectively comprise a rectangular elongated square shape. The embodiment of the container 1 depicted in FIG. 2 can comprise an outlet opening 6 in an upper right corner of the storage compartment 4 and an inlet opening 5 in a lower right corner. A membrane layer strip 7 can extend diagonally from the upper right corner across the storage compartment 4 to the lower left corner of the storage compartment 4. The membrane layer strip 7 can stretch roughly 80% along the diagonal dimension of the container 1 and can cover the outlet opening 6. The membrane layer strip 7 can reach the outermost points of the storage compartment 4, which can be the corners of the square shaped container.

In FIG. 3, the inlet opening 5 and the outlet opening 6 can be positioned next to each other on the center line of the container 1. The outlet opening 6 can be closer to a center of the container 1 and the inlet opening 5 can be closer to the edge of the container 1. The membrane layer can be realized by a widespread membrane layer sheet 8, which can extend in two dimensions along the surface of the storage compartment 4. The membrane layer sheet 7 can cover approximately at least about 50% of the surface of the storage compartment 4. The outlet opening 6 can be covered by the membrane layer sheet 8 and the inlet opening 5 can be located in an uncovered area of the surface of the storage compartment 4.

In FIG. 4, a further embodiment of the container 1 is shown similar to the one of FIG. 3. In contrast to FIG. 3, the membrane layer sheet 8 of the embodiment in FIG. 4 can cover about 80% of the surface of the storage compartment 4. The membrane layer sheet 8 can extend close to the outer edge of the storage compartment 4, except in the area comprising the inlet opening 5 in the lower right corner. The outlet opening 6 and the inlet opening 5 can be positioned next to each other on a line perpendicular to the center line of the container 1.

The inlet and outlet openings 5 and 6 can be arranged according to the demands of a dosing assembly or an automated release device which are using a container 1 as disclosed.

Figure 5A:
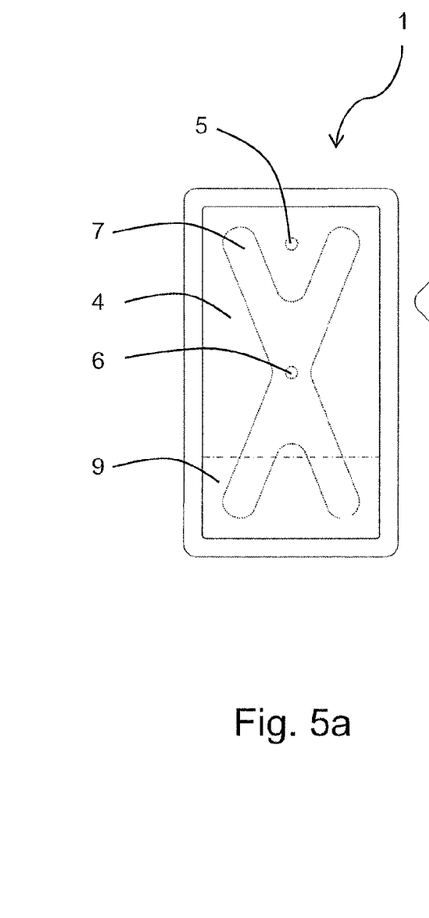
FIG. 5a illustrates top view of a fifth embodiment of a container according to an embodiment of the present disclosure.
Figure 5B:
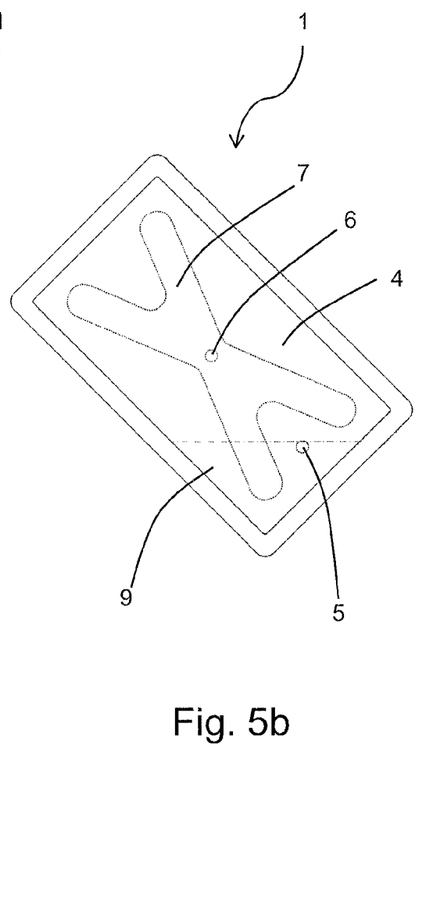
FIG. 5b illustrates top view of the container according to FIG. 5a in a second orientation according to an embodiment of the present disclosure.
Figure 5C:
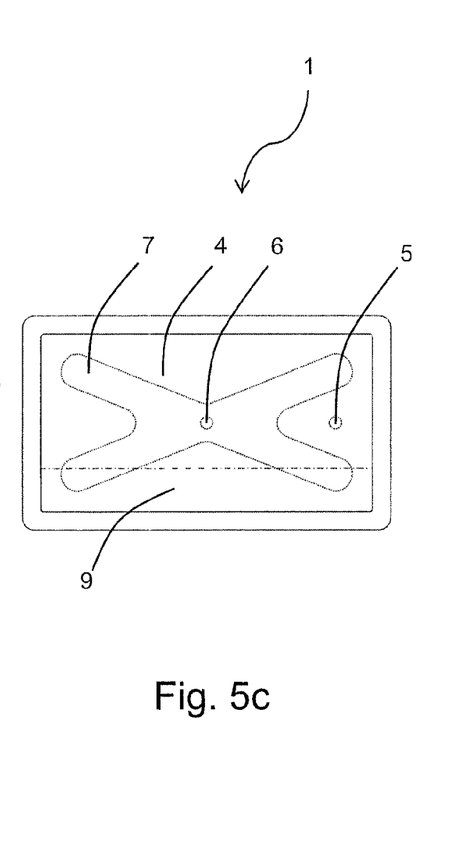
FIG. 5c illustrates top view of the container according to FIG. 5a in a third orientation according to an embodiment of the present disclosure.

In FIGS. 5a-c, a further embodiment of a container 1 is shown. The membrane layer 7 can comprise a cross shaped layout including four membrane layer strip arms, which can run essentially diagonal through the storage compartment 4 and can meet in a crossing point. One membrane layer line can extend diagonal from the upper left corner to the lower right corner of the storage compartment 4 along a first dimension and another membrane layer line can extend form the upper right corner to the lower left corner along a second dimension of the container 1. The membrane layer can alternatively comprise two separate strips crossing each other. Therefore, the membrane layer 7 can reach to the outermost points within the volume of the storage compartment 4. The outlet opening 6 can be located in the middle of the surface of the storage compartment 4, which can correspond to the crossing point of the two membrane layer lines. The inlet opening 5 can be located between the two membrane layer lines close to an edge of the storage compartment 4. The geometry of the membrane layer layout according to this embodiment can offer short distances to the outlet opening 6 from each outermost area of the storage compartment 4 and can avoid a large, spread out membrane surface. The container 1 can be nearly empty and can comprise a substantial amount of air, but the membrane can still be in liquid contact.

In FIG. 5a, the container 1 is shown in a first upright vertical position with the inlet opening 5 in an upper area of the storage compartment 4. The liquid 9 can cover the lower area of the storage compartment 4. Both strips of the membrane layer 7 can extend into the liquid 9. Because of the hydrophilic property of the membrane layer 7, the whole membrane layer can be saturated with liquid 9 and the liquid 9 can be transported to the outlet opening 6 within the membrane layer 7. The flow of the liquid 9 along the membrane layer 7 can be forced by pump system, for example, of a dosing assembly of an automated release device.

In FIG. 5b, the container 1 can be turned about 135° to the right into an oblique orientation. In this position, a corner of the container 1 can be the lowest point of the storage compartment 4 and only a part of only one strip of the membrane layer 7 can extend into the liquid 9. Even in this extreme orientation, the membrane layer 7 can be sucked with liquid 9 and can deliver liquid 9 to the outlet opening 6. In FIG. 5c, the container 1 can be turned about 90° to the right in relation to the position of FIG. 5a into a horizontal orientation. Again, two parts of the membrane layer 7 can reach into the liquid 9 and can wet the whole membrane layer 7 such that liquid 9 can flow to the outlet opening 6.

As illustrated in FIGS. 5a to 5c, the membrane layer 7 can be in contact with liquid 9 irrespective of the orientation of the container 1. Therefore, the membrane layer 7 can hold back air bubbles enclosed in the storage compartment 4 in any arbitrary position of the container 1. This can offer a user of the container and a dosing assembly or automated release device comprising such a container a high degree of flexibility in choosing a preferred position on the body without delimiting the function of such an assembly or device.

Figure 6A:
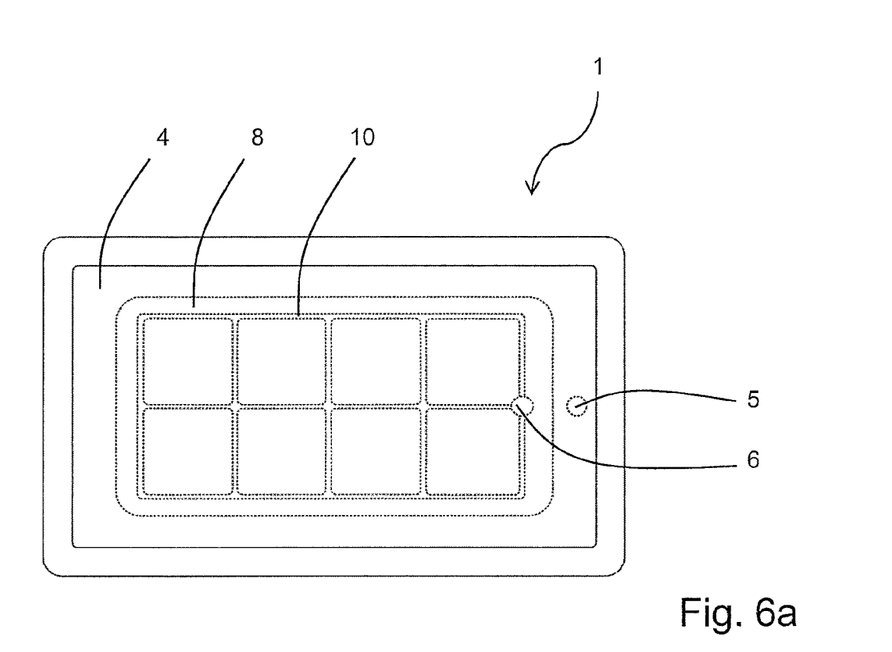
FIG. 6a illustrates top view the third embodiment of a container comprising a channel structure according to an embodiment of the present disclosure.
Figure 6B:
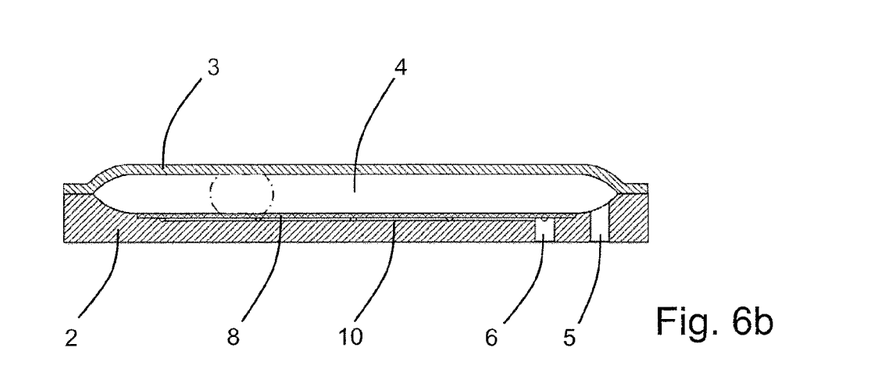
FIG. 6b illustrates cross-sectional side view of the container according to FIG. 6a according to an embodiment of the present disclosure.

In FIGS. 6a and 6b, an embodiment of the container 1 similar to the one shown in FIG. 3 is shown. Additionally, the container 1 can comprise a channel structure 10 in form of a channel network between the membrane layer sheet 8 and a surface of the storage compartment 4 to which the membrane layer 8 can be attached. The channel structure network 10 can spread out over the full size of the membrane layer sheet 8 in a square pattern and can end at the outlet opening 6. The membrane layer sheet 8 can cover the whole channel structure 10 and can be sealed at the edge to the surface of the storage compartment 4 such that the channel structure 10 can be separated from the storage compartment volume in a gas-tight manner. As can be seen in FIG. 6b, the channel structure network can be realized by longitudinal grooves embedded into the surface of the rigid wall part 3 below the membrane layer 7. The channel structure 10 can assist liquid passed through the membrane layer 7 to flow to the outlet opening 6. Alternatively to a grooved channel structure the porosity of the hydrophilic membrane layer 7 can advantageously be used as a channel structure. The pores of the membrane can be connected such that a passage way through the membrane can reach from the storage compartment to the outlet opening.

Figure 7A:
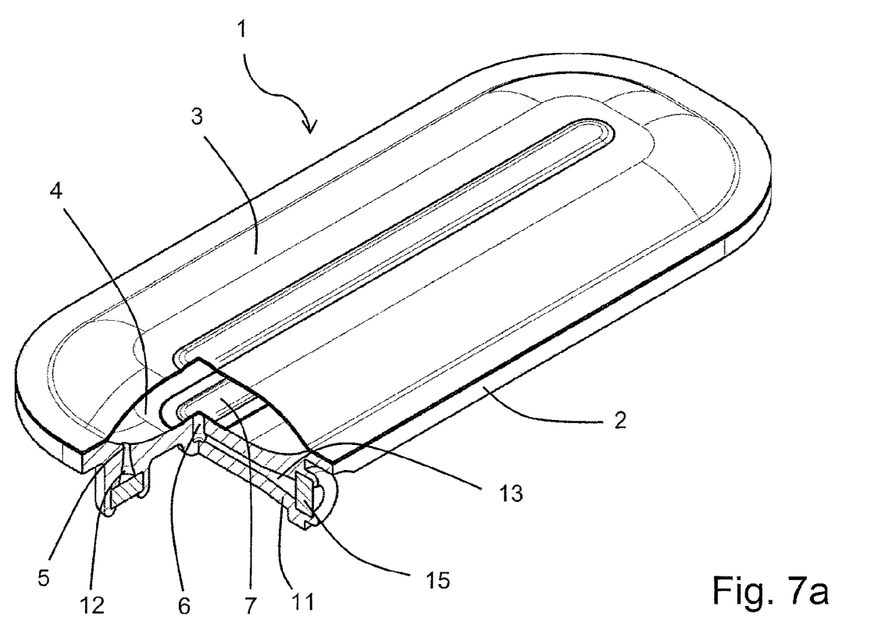
FIG. 7a illustrates three-dimensional cutout view of a further embodiment of a container comprising an inlet port and an outlet port according to an embodiment of the present disclosure.
Figure 7B:
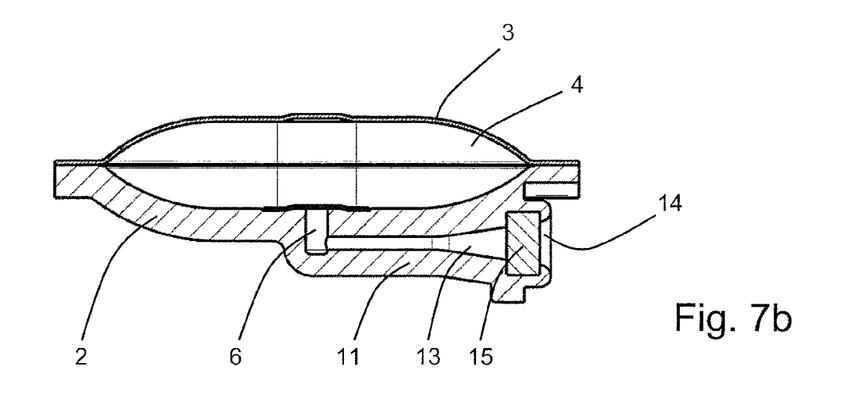
FIG. 7b illustrates cross-sectional side view of the container according to FIG. 7a according to an embodiment of the present disclosure.

FIGS. 7a and 7b show still a further embodiment of a container 1 comprising a first connection port 11 at the outlet opening 6 and a second connection port 12 at the inlet opening 5. The membrane layer layout can correspond the container embodiment of FIGS. 1a and 1b comprising an elongated membrane layer strip 7 along a longitudinal axis of the storage compartment 4. The flexible wall sheet 3 can arch over the rigid wall part 2. As illustrated in FIG. 7b, the outlet connection port 11 can be integrated in the rigid wall part 3 and can be realized by a conduit 13 connected to the outlet opening 6. The conduit 13 can terminate at the outer edge of the rigid wall part 2 in an adapter opening 14 suitable for attaching a connection device of a dosing assembly and/or a device for automated release of a liquid. The adapter opening 14 can be closed by a septum 15, which can be pierced by a needle of the dosing assembly or the automated release device. The connection device can for example be attached to the adapter opening 14 by a press fitting or the like. Of course other variations of connection ports can be realized with a container as disclosed. In the figures, the container is shown in a filled state. As it is emptied, the flexible wall sheet 3 can bend inwards and can contact the rigid wall part 2 when empty.

Figure 8A:
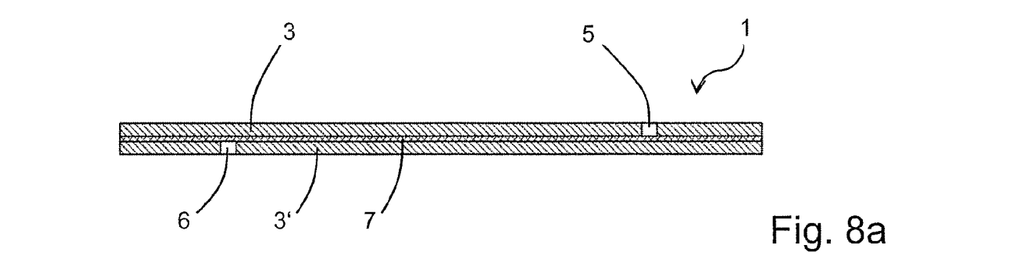
FIG. 8a illustrates cross-sectional side view of still a further embodiment of a container in an empty state according to an embodiment of the present disclosure.
Figure 8B:
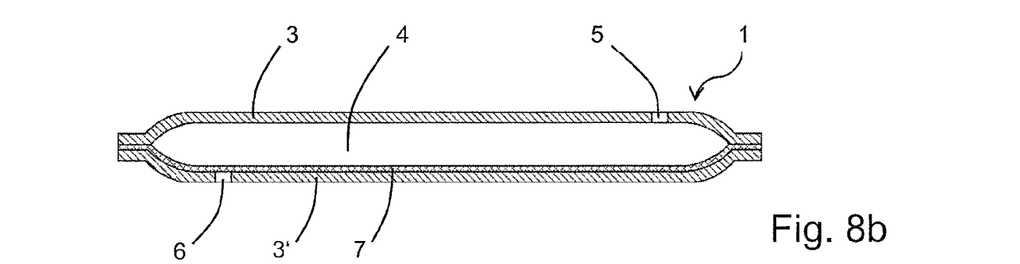
FIG. 8b illustrates cross-sectional side view of the container according to FIG. 8a in a filled state according to an embodiment of the present disclosure.

FIGS. 8a to 8d illustrate an embodiment of a container comprising two flexible wall sheets 3 and 3'. The first flexible wall sheet 3 can comprise the inlet opening 5 and the second flexible wall sheet 3' can comprise the outlet opening 6. The two flexible wall sheets 3 and 3' can be sealed together at their circumferential edge, while the membrane layer 7 can also be sealed to the flexible wall sheet 3 in the sealing area of the sheets such that the membrane layer can be sandwiched between the sheets 3, 3' at their circumferential edge. Thus, the liquid in the storage compartment can be separated from the outlet opening 6. In FIG. 8a, the container 1 is shown in an empty state before filling of a medical or pharmaceutical liquid. In FIG. 8b, the same container 1 is shown after filling of the storage compartment 4 with a liquid. The first flexible wall sheet 3 and the second flexible wall sheet 3' can be lifted off each other in their middle parts. As soon as liquid is filled into the storage compartment 4, the membrane layer 7 can suck liquid and can be able to prevent air from passing through the membrane in direction of the outlet opening 6.

Figure 8C:
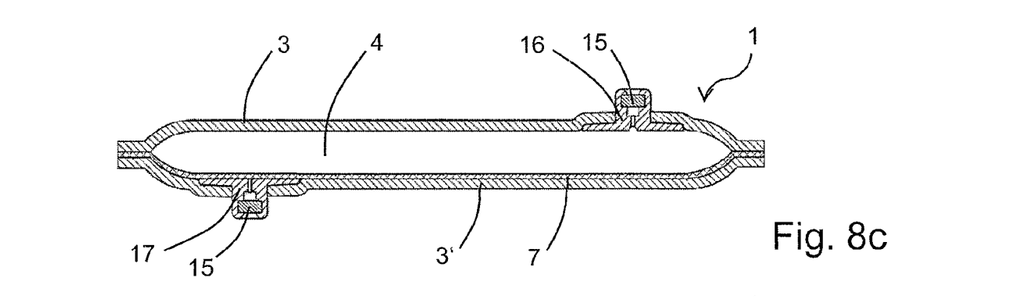
FIG. 8c illustrates cross-sectional side view of a first alternative of the container according to FIG. 8a according to an embodiment of the present disclosure.

In FIG. 8c, a first alternative of the container according to FIGS. 8a and 8b is shown comprising an inlet connection port piece 16 within the inlet opening 5 and an outlet connection port piece 17 within the outlet opening 6. The inlet and outlet connection port pieces 16 and 17 can be closed by a septum 15. The pieces 16 and 17 may be identical ports made of hard units, which can be inserted into the inlet and outlet openings before sealing the first and second flexible wall sheets 3 and 3'.

In FIGS. 8a to 8c, the inlet opening 5 can be positioned diagonal opposite to the outlet opening 6. Such liquid inserted through the inlet opening 5 can pass the maximal possible distance to the outlet opening 6.

Figure 8D:
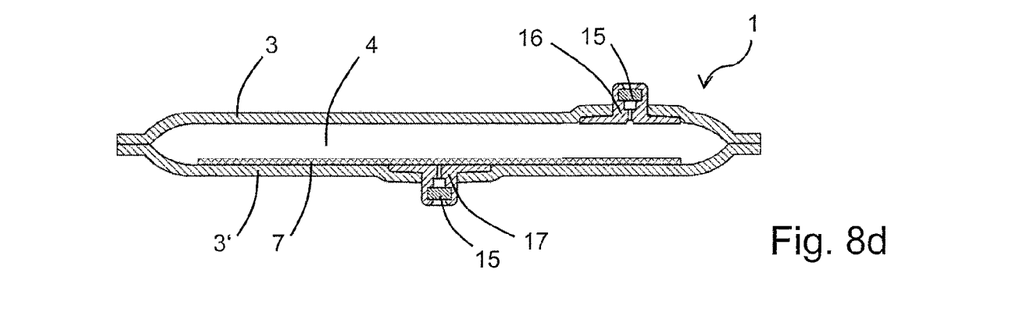
FIG. 8d illustrates cross-sectional side view of a second alternative of the container according to FIG. 8a according to an embodiment of the present disclosure.

In FIG. 8d, an alternative to the embodiment of FIGS. 8a to 8c is shown. The outlet opening 6 can be located in a center area of the second flexible wall sheet 3' and membrane layer 6 can be attached directly to the flexible wall sheet 3'. This can add flexibility and, in particular, can allow the membrane layer 7 to be smaller and not to cover the whole area of the layer 3'. In addition, it can allow the inlet opening to be arranged an the same wall sheet 3' as the outlet opening, in embodiment, in a cut-out of the membrane layer 7. In this alternative, liquid can flow only a short distance from every section within the storage compartment 4 to the outlet opening 6.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "essentially" is utilized herein to represent the inherent degree of uncertainty that may be attributed to any quantitative comparison, value, measurement, or other representation. The term "essentially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. In particular the features of the container may be adapted in respect to specific demands of a dosing assembly and/or a device for automated release of a medical or pharmaceutical liquid according to the invention.

We claim:

1. A container for storing a medical or pharmaceutical liquid, the container comprising:
   a storage compartment for storing the liquid comprising an outlet opening for discharging liquid out of the storage compartment, wherein the container is sealed to store the liquid before use;
   a hydrophilic membrane layer within the storage compartment which is gas-tight in a wet condition and covers the outlet opening, wherein the hydrophilic membrane layer is configured to contact the liquid stored within the storage compartment independent of a container orientation with respect to gravity and a filling level of the container;
   wherein the storage compartment has an inner surface that has the outlet opening;
   wherein the hydrophilic membrane layer is attached to the inner surface; and
   at least one flexible wall sheet positioned opposite the inner surface to collapse towards the inner surface as the liquid is discharged out of the storage compartment.

2. The container according to claim 1, wherein the membrane layer extends at least along 50% of a length of the storage compartment in at least one dimension.

3. The container according to claim 1, wherein a membrane layer layout within the storage compartment comprises a straight, diagonal, waved, annulated, and/or zigzag geometry and/or a cross or star shaped geometry.

4. The container according to claim 1, wherein the membrane layer comprises at least one membrane strip running along a center line of an inner surface of the storage compartment.

5. The container according to claim 1, wherein a membrane layer layout comprises a cross shaped geometry running diagonal through the storage compartment and contains a cross point in a middle area of the storage compartment.

6. The container according to claim 1, wherein the hydrophilic membrane layer is made of porous membrane material.

7. The container according to claim 6, wherein a pore size of the porous membrane material varies within the membrane layer.

8. The container according to claim 1, wherein the storage compartment comprises an essentially rigid wall part comprising the outlet opening.

9. The container according to claim 1, further comprises, wherein the at least one flexible wall sheet includes two flexible wall sheets sealed together such that the storage compartment is encompassed by the flexible wall sheets.

10. The container according to claim 1, wherein a channel structure is arranged in or on the inner surface of the storage compartment to which the membrane layer is attached and wherein the channel structure is in fluid connection with the outlet opening.

11. The container according to claim 1, wherein a channel structure is realized by a porous structure of the membrane layer.

12. The container according to claim 1, wherein a connection port in fluid connection to the outlet opening is arranged on an outer side of the container.

13. The container according to claim 1, wherein the container is applied in a dosing assembly and/or release device and wherein a pore size of the membrane layer of the container is dimensioned such that, during application, a differential pressure over the membrane layer is below a bubble pressure of the membrane layer.

14. The container according to claim 1, wherein the hydrophilic membrane is attached flush to the inner surface.

15. The container according to claim 1, wherein:
the storage compartment includes a rigid wall part that defines the inner surface and the outlet opening;
the storage compartment is at least defined between the rigid wall part and the at least one flexible wall sheet; and
wherein the at least one flexible wall sheet is configured to collapse towards the inner surface with the hydrophilic membrane as the liquid is discharged out of the storage compartment.

16. The container according to claim 1, wherein:
the storage compartment has corners;
the hydrophilic membrane is attached flush to the inner surface; and
the hydrophilic membrane extends from the outlet opening to at least one of the corners.

17. The container according to claim 1, wherein a greater middle area of the hydrophilic membrane layer remains in flush contact with the inner surface to serve as a contact area for the liquid.

18. A dosing assembly, the dosing assembly comprising:
at least one container according to claim 1; and
a dosing unit, wherein the outlet opening of the at least one container is, during application, in fluidic connection with the dosing unit.

19. A device for automated release of a medical or pharmaceutical liquid, comprising the at least one dosing assembly according to claim 18, the device further comprising:
control circuitry; and
a drive unit coupled to the container or the dosing assembly during application, wherein the control circuitry is operatively coupled to the drive unit, thus controlling automated drug release of the container.

20. A container for storing a medical or pharmaceutical liquid, the container comprising:
a storage compartment for storing the liquid comprising an outlet opening for discharging liquid out of the storage compartment;
a hydrophilic membrane layer within the storage compartment which is gas-tight in a wet condition and covers the outlet opening, wherein the hydrophilic membrane layer is configured to contact the liquid stored within the storage compartment independent of a container orientation with respect to gravity and a filling level of the container;
wherein the storage compartment has an inner surface that has the outlet opening;
wherein the hydrophilic membrane layer is attached to the inner surface;
at least one flexible wall sheet positioned opposite the inner surface to collapse towards the inner surface as the liquid is discharged out of the storage compartment; and
wherein the at least one flexible wall sheet includes two flexible wall sheets sealed together such that the storage compartment is encompassed by the flexible wall sheets.

\* \* \* \* \*